(12) United States Patent
Lefevre et al.

(10) Patent No.: US 11,026,658 B2
(45) Date of Patent: Jun. 8, 2021

(54) DEVICE FOR POSITIONING A MARKER IN A 3D ULTRASONIC IMAGE VOLUME

(71) Applicant: KONINKLIJKE PHILIPS N.V., Eindhoven (NL)

(72) Inventors: Thierry Lefevre, Eindhoven (NL); Pascal Yves Francois Cathier, Eindhoven (NL); Cybele Ciofolo-Veit, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 464 days.

(21) Appl. No.: 15/549,824

(22) PCT Filed: Feb. 3, 2016

(86) PCT No.: PCT/EP2016/052212
§ 371 (c)(1),
(2) Date: Aug. 9, 2017

(87) PCT Pub. No.: WO2016/131648
PCT Pub. Date: Aug. 25, 2016

(65) Prior Publication Data
US 2018/0021020 A1 Jan. 25, 2018

(30) Foreign Application Priority Data
Feb. 17, 2015 (EP) .................................... 15305237

(51) Int. Cl.
*A61B 8/08* (2006.01)
*A61B 90/00* (2016.01)
(Continued)

(52) U.S. Cl.
CPC ............ *A61B 8/483* (2013.01); *A61B 8/0841* (2013.01); *A61B 90/37* (2016.02); *A61B 8/464* (2013.01);
(Continued)

(58) Field of Classification Search
CPC ....... A61B 8/483; A61B 8/0841; A61B 8/464; A61B 90/37; A61B 2090/378;
(Continued)

(56) References Cited

U.S. PATENT DOCUMENTS 6,064,904 A 5/2000 Yanof
6,216,029 B1 4/2001 Paltieli
(Continued)

FOREIGN PATENT DOCUMENTS

WO 0133251 A1 5/2001

*Primary Examiner* — Peter Luong

(57) ABSTRACT

The invention relates to a device (1) for positioning a marker (2) in a 3D ultrasonic image volume (3), a system for positioning a marker (2) in a 3D ultrasonic image volume (3), a method for positioning a marker (2) in a 3D ultrasonic image volume (3), a computer program element for controlling such device (1) for performing such method and a computer readable medium having stored such computer program element. The device (1) comprises an image provision unit (11), a marker unit (12) and a display unit (13). The image provision unit (11) is configured to provide a 3D ultrasonic image volume (3) showing an object (4). The marker unit (12) is configured to position a marker (2) in the 3D ultrasonic image volume (3). The display unit (13) is configured to display the 3D ultrasonic image volume (3) and the marker (2) in a first imaging view (31) in a first imaging plane and in a second imaging view (32) in a second, different imaging plane. The positioning of the marker (2) is limited to be on a projection line (5). The first and the second imaging views are rotated relative to each other, so that the projection line (5) has a first angle relative to the first imaging plane and a second, different angle relative to the second imaging plane.

6 Claims, 3 Drawing Sheets

(51) Int. Cl.
 *A61B 8/00* (2006.01)
 *A61B 34/10* (2016.01)

(52) U.S. Cl.
 CPC ... *A61B 2034/107* (2016.02); *A61B 2090/364* (2016.02); *A61B 2090/378* (2016.02); *A61B 2090/3925* (2016.02)

(58) Field of Classification Search
 CPC ...... A61B 2090/364; A61B 2090/3925; A61B 2034/107
 See application file for complete search history.

(56) References Cited

U.S. PATENT DOCUMENTS

| | | |
|---|---|---|
| 6,336,899 B1 | 1/2002 | Yamazaki |
| 6,379,302 B1 | 4/2002 | Kessman et al. |
| 2001/0007917 A1 | 7/2001 | Hayakawa et al. |
| 2004/0215071 A1 | 10/2004 | Frank et al. |
| 2005/0033160 A1* | 2/2005 | Yamagata ................ A61B 6/12 600/425 |
| 2010/0298704 A1 | 11/2010 | Pelissier et al. |
| 2012/0143045 A1 | 6/2012 | Klingenbeck |
| 2013/0345718 A1* | 12/2013 | Crawford ........... A61B 17/7082 606/130 |
| 2014/0071132 A1 | 3/2014 | Noshi et al. |
| 2015/0302634 A1 | 10/2015 | Florent et al. |

* cited by examiner

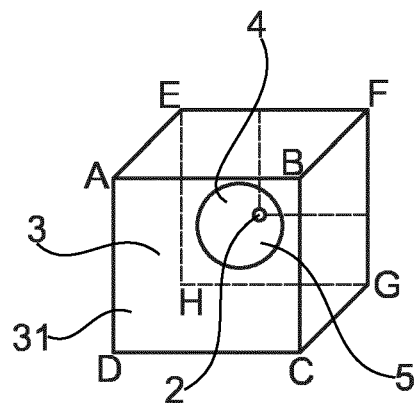
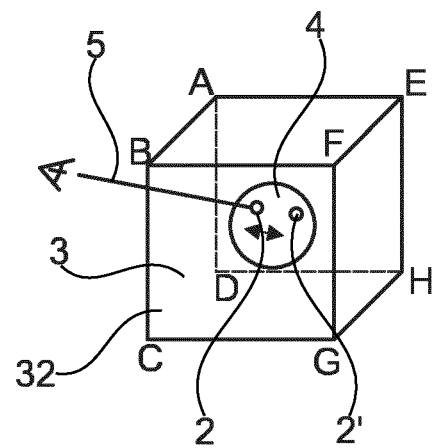
Fig. 2a    Fig. 2b
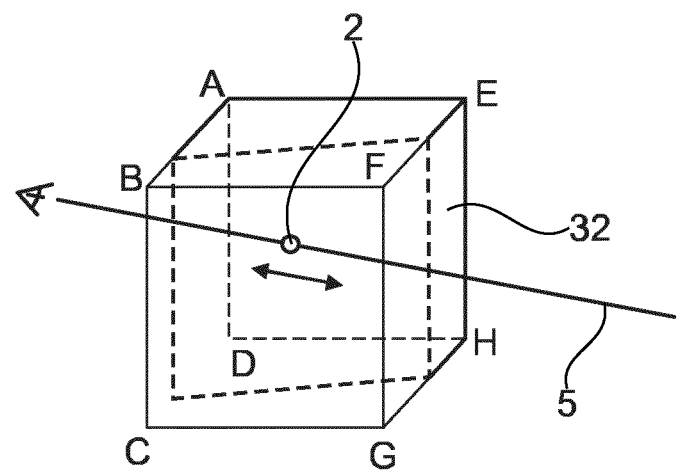
Fig. 3

DEVICE FOR POSITIONING A MARKER IN A 3D ULTRASONIC IMAGE VOLUME

This application is the U.S. National Phase application under 35 U.S.C. § 371 of International Application No. PCT/EP2016/052212, filed on Feb. 3, 2016, which claims the benefit of EP Application Serial No. 15305237.8, filed Feb. 17, 2015. These applications are hereby incorporated by reference herein.

FIELD OF THE INVENTION

The invention relates to a device for positioning a marker in a 3D ultrasonic image volume, a system for positioning a marker in a 3D ultrasonic image volume, a method for positioning a marker in a 3D ultrasonic image volume, a computer program element for controlling such device for performing such method and a computer readable medium having stored such computer program element.

BACKGROUND OF THE INVENTION

For image-guided medical, in particular surgical procedures, often 3D ultrasound imaging is used. For example, WO 01/33251 (A1) discloses such ultrasonic diagnostic imaging system. An advantage of 3D ultrasound imaging is that it can be used in real-time during the surgical procedure. In e.g. cardiological procedure, trans-esophageal probes can be navigated right next to the heart, producing real-time volumetric images with anatomical details that are hardly visible with standard transthoracic ultrasound. A typical intervention is percutaneous valve repair (PVR) such as mitral clipping where 3D ultrasound imaging has been found helpful to monitor the placement of the tool/endoprosthesis with respect to the soft-tissue anatomy.

SUMMARY OF THE INVENTION

There may be a need to provide an improved device for positioning a marker in a 3D ultrasonic image volume, which makes the positioning of the marker convenient for a user.

The problem of the present invention is solved by the subject-matters of the independent claims, wherein further embodiments are incorporated in the dependent claims. It should be noted that the aspects of the invention described in the following apply also to the device for positioning a marker in a 3D ultrasonic image volume, the system for positioning a marker in a 3D ultrasonic image volume, the method for positioning a marker in a 3D ultrasonic image volume, the computer program element, and the computer readable medium.

According to the present invention, a device for positioning a marker in a 3D ultrasonic image volume is presented. The device comprises an image provision unit, a marker unit and a display unit. The image provision unit is configured to provide a 3D ultrasonic image volume showing an object. The marker unit is configured to position a marker in the 3D ultrasonic image volume. The display unit is configured to display the 3D ultrasonic image volume and the marker in a first imaging view in a first imaging plane and in a second imaging view in a second, different imaging plane. The positioning of the marker is limited to be on a projection line. The first and the second imaging views are rotated relative to each other, so that the projection line has a first angle relative to the first imaging plane and a second, different angle relative to the second imaging plane.

Thereby, the device for positioning a marker in a 3D ultrasonic image volume according to the present invention provides a convenient way to place and/or replace a 3D marker in a scene. For example, the marker may be placed on an object's surface and may then be replaced to another point lying "behind" the object's surface and therefore within or behind the object. In other words, the marker unit may be configured to position the marker in the first ultrasonic image data in a first position and to reposition the marker in the second ultrasonic image data into a second, different position. The marker unit may be configured to position the marker in the first imaging view in a first position on a surface of the object and to reposition the marker in the second imaging view in a second position in the volume of the object. The first and second imaging views belong to one and the same 3D volume and are seen from different viewpoints. The 3D ultrasonic image volume can be static 3D or 3D video. The latter means, the volume can change depending on the time, which is sometimes also referred to as 4D data. The object may be a body part.

The positioning and repositioning of the marker is limited to a projection line, in other words, the marker can only slide along the projection line. Thereby, depth ambiguity when trying to position a 3D point using a single view is overcome. This is achieved in that the same 3D ultrasonic image volume is shown to the user in two different imaging views which are rotated relative to each other. Thereby, the projection line is shown with two different angles. In other words, the projection line extends in the first imaging view in a first direction and in the second imaging view in a second, different direction.

For example, in a first imaging view, the projection line may be displayed as a point or dot, and in the second imaging view as a straight or line. In the second imaging view, it is a lot easier for the user to move the marker along the line-shaped projection line than handling the point-shaped projection line in the first imaging view. The projection line may be defined using two points in 3D. By default, these two points could be the position of a virtual camera in 3D and a point at a surface of an object e.g. selected by the user. With this default setting, the projection line will appear as a point, thus requiring rotating the view. The virtual camera is a virtual location in 3D of a camera viewing the volume. In other words, in a first view, the projection line is aligned with the camera, in the second view it is not.

It is further possible to remove (or make transparent) an element of the scene that hides or covers the projection line by cropping the volume using a vertical plane passing through the projection line. In other words, the marker unit may be configured to crop a volume of the second imaging view to cut out an element covering the projection line. The marker unit may be further configured to crop the volume by means of a plane crossing the projection line. Thereby, the view is cleared to help the positioning of the marker.

In an example, the modification between the first and the second imaging view is a rigid transformation. In an example, the modification between the first and the second imaging view comprises a translation. In an example, the modification between the first and the second imaging view comprises a magnification or scaling. This means, the rotation between the first and second imaging views may further comprise a translation and/or a magnification.

There are several alternatives for the user to control the device according to the present invention. A user can click on a button to rotate a first view after positioning a marker. In a second, rotated view, the user can slide the marker along a projection line. Once the marker is in a correct or predefined position, the user may click the button again to come back to the original, first view.

Alternatively, the user can hold down the click to rotate the view when positioning the marker in 3D. In the second, rotated view, the point can slide along the projection line as long as the click is hold down. Then, the second view can come back to the original, first view. Also other alternatives are possible.

According to the present invention, also a system for positioning a marker in a 3D ultrasonic image volume is presented. It comprises a device as described above and an ultrasonic probe which supplies data to the image provision unit of the device.

According to the present invention, also a method for positioning a marker in a 3D ultrasonic image volume is presented. It comprises the following steps, not necessarily in this order:

a) providing a 3D ultrasonic image volume showing an object,
b) positioning a marker in the 3D ultrasonic image volume, wherein the positioning of the marker is limited to be on a projection line, and
c) displaying the 3D ultrasonic image volume and the marker in a first imaging view in a first imaging plane and in a second imaging view in a second, different imaging plane.

The first and the second imaging views are rotated relative to each other, so that the projection line has a first angle relative to the first imaging plane and a second, different angle relative to the second imaging plane.

In an example, the method further comprises a cropping of a volume of the second imaging view to cut out an element covering the projection line. The volume may be cropped by means of a plane crossing the projection line. Thereby, the view is cleared to help the positioning of the marker.

According to the present invention, also a computer program element is presented, wherein the computer program element comprises program code means for causing the device as defined in the independent claim to carry out the steps of the method as defined in the independent claim when the computer program is run on a computer controlling the device.

It shall be understood that the device, the method, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings:

FIG. 2 shows schematically and exemplarily a positioning of a marker in the 3D ultrasonic image volume.

FIG. 3 shows also schematically and exemplarily a positioning of a marker in the 3D ultrasonic image volume.

DETAILED DESCRIPTION OF EMBODIMENTS

Figure 1:
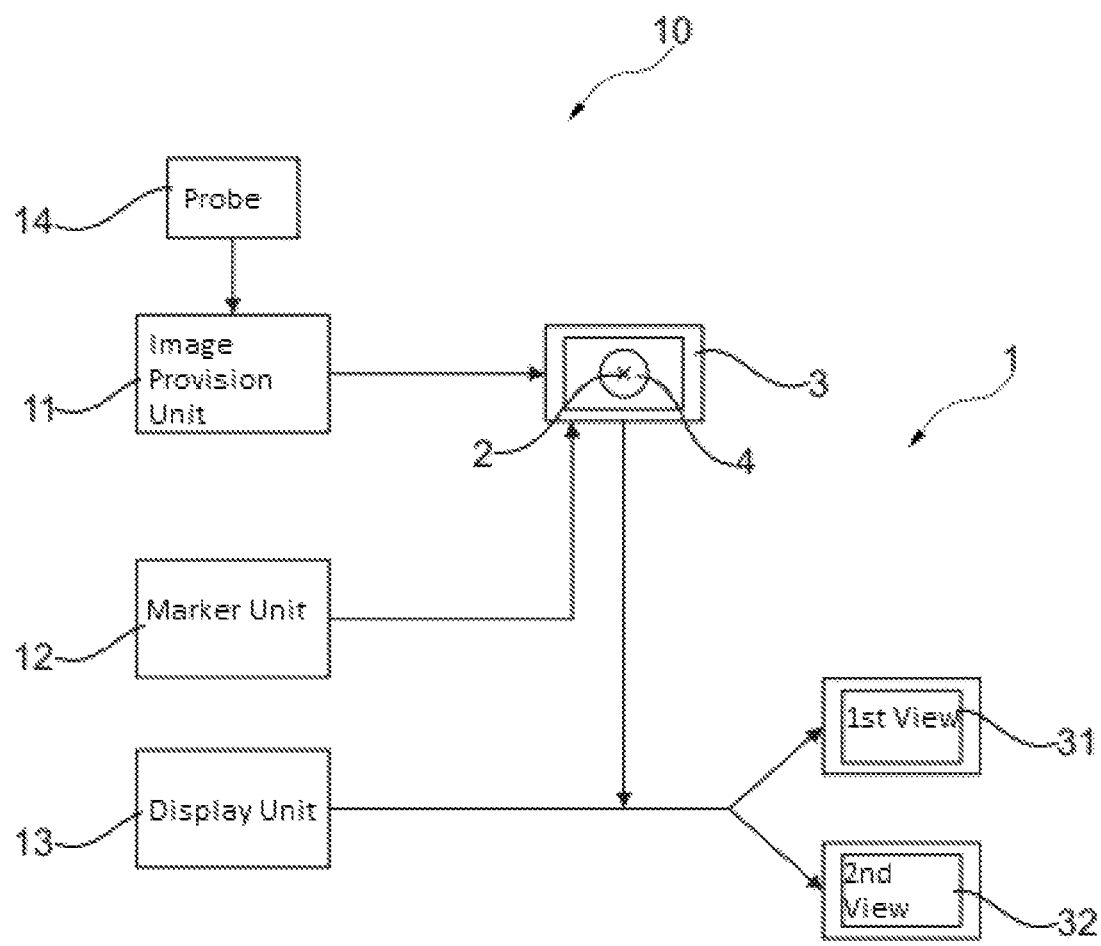
FIG. 1 shows a schematic drawing of an example of a device for positioning a marker in a 3D ultrasonic image volume.

FIG. 1 shows schematically and exemplarily an embodiment of a system 10 for positioning a marker in a 3D ultrasonic image volume. It comprises a device as described in detail below and an ultrasonic probe 14 which supplies data to an image provision unit 11 of the device 1. FIG. 1 further shows the device 1 for positioning a marker 2 in a 3D ultrasonic image volume 3 according to the invention (see also FIG. 2). The device 1 comprises the image provision unit 11, a marker unit 12 and a display unit 13. The image provision unit 11 provides a 3D ultrasonic image volume 3 showing an object 4. The object 4 is here a body part. The marker unit 12 positions a marker 2 in the 3D ultrasonic image volume 3. The display unit 13 displays the 3D ultrasonic image volume 3 and the marker 2 in a first imaging view 31 in a first imaging plane and in a second imaging view 32 in a second, different imaging plane. The positioning of the marker 2 is limited to be on a projection line 5. The projection line 5 may be defined to be between an ultrasonic probe and the object 4.

As shown in FIG. 2a, the marker 2 can be placed on an object's surface and can then be replaced, as shown in FIG. 2b, to another point 2' lying "behind" the object's surface and therefore within or behind the object 4. In other words, the marker unit 12 positions the marker 2 in the first ultrasonic image data in a first position (FIG. 2a) and repositions the marker 2 in the second ultrasonic image data into a second, different position (FIG. 2b). Here, the marker unit 12 positions the marker 2 in the first imaging view 31 in a first position on a surface of the object 4 and repositions the marker 2 in the second imaging view 32 in a second position in the volume of the object 4.

The positioning and repositioning of the marker 2 is limited to the projection line 5, in other words, the marker 2 can only slide along the projection line 5. The depth ambiguity is overcome as the projection line 5 is shown with two different angles. In this example, in the first imaging view 31 (FIG. 2a), the projection line 5 is displayed as a point or dot, and in the second imaging view 32 (FIG. 2b) as a straight or line. In the second imaging view 32, it is a lot easier for the user to move the marker 2 along the projection line 5 than handling the point-shaped projection line 5 in the first imaging view 31. The projection line may be defined using two points in 3D. By default, these two points could be the position of a virtual camera in 3D and a point at a surface of an object e.g. selected by the user. The virtual camera is a virtual location in 3D of a camera viewing the volume. With this default setting, the projection line will appear as a point, thus requiring rotating the view. In other words, in a first view, the projection line is aligned with the camera, in the second view it is not. In the example of FIG. 2, the projection line 5 has a first angle of 90° (degrees) relative to the first imaging plane of the first imaging view 31 and a second, different angle of e.g. 0° (degrees) relative to the second imaging plane of the second imaging view 32.

As a summary, the first and the second imaging views are rotated relative to each other, so that the projection line 5 has a first angle relative to the first imaging plane and a second, different angle relative to the second imaging plane. Thereby, a convenient way to place and/or replace a 3D marker 2 in a scene is provided. The rotation between the first and second imaging views may further comprise a translation and/or a magnification.

In other words, FIGS. 2a and 2b illustrate and solves the depth ambiguity when trying to position a 3D point using a single view. It is unknown where the maker 2 should be along the projection line 5, therefore the maker 2 is placed at the first surface crossed by the projection line 5, which is the object's surface. In detail, a point in FIG. 2a actually corresponds to a line in FIG. 2b. In FIG. 2a, the two points 2 and 2' are mingled, which is the reason why the projection line 5 appears as a single point. However, in FIG. 2b, the two points 2 and 2' are distinct and the projection line 5 "really" appears as a line. The dashed lines represent the intersection between the projection line 5 and the faces ABCD and EFGH of the shown cubes.

As shown in FIG. 3, an element of the scene that e.g. hides or covers the projection line 5 can be removed by cropping or cutting the volume using a vertical plane passing through the projection line 5. In other words, the marker unit 12 crops the volume of the second imaging view 32 to cut out the element covering the projection line 5. Thereby, the view is cleared to help the positioning of the marker 2.

Figure 4:
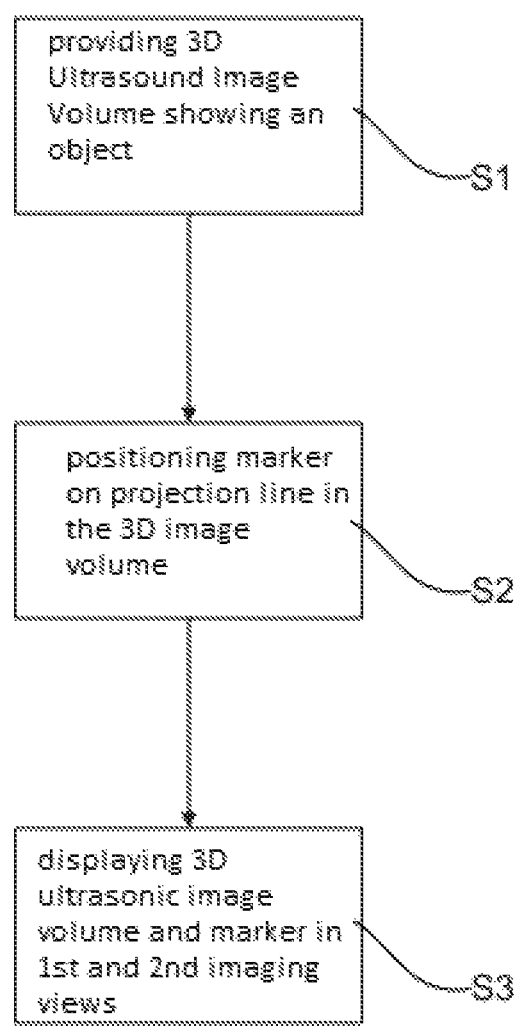
FIG. 4 shows basic steps of an example of a method for positioning a marker in a 3D ultrasonic image volume.

FIG. 4 shows a schematic overview of steps of a method for positioning a marker 2 in a 3D ultrasonic image volume 3. The method comprises the following steps, not necessarily in this order:

In a first step S1, providing a 3D ultrasonic image volume 3 showing an object 4.
In a second step S2, positioning a marker 2 in the 3D ultrasonic image volume 3, wherein the positioning of the marker 2 is limited to be on a projection line 5.
In a third step S3, displaying the 3D ultrasonic image volume 3 and the marker 2 in a first imaging view 31 in a first imaging plane and in a second imaging view 32 in a second, different imaging plane.

The first and the second imaging views are rotated relative to each other, so that the projection line 5 has a first angle relative to the first imaging plane and a second, different angle relative to the second imaging plane.

The method further comprises a cropping of a volume of the second imaging view 32 to cut out an element covering the projection line 5. The volume may be cropped by means of a plane crossing the projection line 5. Thereby, the view is cleared to help the positioning of the marker 2.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for positioning a marker in a 3D ultrasonic image volume, comprising:
a processor: and
a display unit,
wherein the processor is configured to provide a 3D ultrasonic image volume showing an object,
wherein the processor is configured to position a marker in the 3D ultrasonic image volume,
wherein the display unit is configured to display the 3D ultrasonic image volume and the marker in a first 3D imaging view in a first imaging plane and in a second 3D imaging view in a second, different imaging plane, wherein the positioning of the marker is limited to be on a projection line, wherein the first and the second 3D imaging views are rotated relative to each other, so that the projection line has a first angle relative to the first imaging plane and a second, different angle relative to the second imaging plane, and wherein the processor is configured to crop a volume of the second 3D imaging view to cut out an element covering the projection line.

2. The device according to claim 1, wherein the processor is configured to position the marker in the second 3D imaging view in the volume of the object.

3. The device according to claim 1, wherein the processor is configured to position the marker in the first 3D imaging view in a first position on a surface of the object and to reposition the marker in the second 3D imaging view in a second position in the volume of the object.

4. The device according to claim 1, wherein the processor is further configured to crop the volume by means of a plane crossing the projection line.

5. A system for positioning a marker in a 3D ultrasonic image volume, comprising:

a device according to claim 1, and an ultrasonic probe, wherein the ultrasonic probe supplies data to an image provision unit of the device.

6. A method for positioning a marker in a 3D ultrasonic image volume comprising the following steps:

a) providing a 3D ultrasonic image volume showing an object, b) positioning a marker in the 3D ultrasonic image volume, wherein the positioning of the marker is limited to be on a projection line, and c) displaying the 3D ultrasonic image volume and the marker in a first 3D imaging view in a first imaging plane and in a second 3D imaging view in a second, different imaging plane, wherein the first and the second 3D imaging views are rotated relative to each other, so that the projection line has a first angle relative to the first imaging plane and a second, different angle relative to the second imaging plane, and d) cropping of a volume of the second 3D imaging view to cut out an element covering the projection line.

* * * * *